United States Patent [19]

Ikeyama

[11] Patent Number: 4,664,127
[45] Date of Patent: May 12, 1987

[54] VEHICLE-LOADED HEARTBEAT METER
[75] Inventor: Takeshi Ikeyama, Tokyo, Japan
[73] Assignee: Aisin Seiki Kabushiki Kaisha, Japan
[21] Appl. No.: 770,042
[22] Filed: Aug. 28, 1985
[30] Foreign Application Priority Data Aug. 28, 1984 [JP] Japan .................................. 59-178588

[51] Int. Cl.$^4$ ................................................ A61B 5/04
[52] U.S. Cl. ................................................... 128/689
[58] Field of Search ................ 128/687, 689; 340/505, 340/526, 575, 576

[56] References Cited

U.S. PATENT DOCUMENTS

| | | | |
|---|---|---|---|
| 2,848,712 | 8/1958 | Preston | 340/575 |
| 3,082,414 | 3/1963 | Papaminas | 128/687 |
| 3,106,981 | 10/1963 | Chakiris | 340/576 |
| 3,561,430 | 2/1971 | Filler, Jr. | 128/661 |
| 3,793,626 | 2/1974 | Zambato | 340/526 |
| 3,794,969 | 2/1974 | Klopfenstein | 340/576 |
| 3,858,574 | 1/1975 | Page | 128/689 |
| 3,877,541 | 4/1975 | Takeuchi et al. | 340/576 |
| 3,913,086 | 10/1975 | Adler et al. | 340/576 |
| 3,947,811 | 3/1976 | Hodgson | 340/505 |
| 3,996,928 | 12/1976 | Marx | 128/687 |
| 4,125,111 | 11/1978 | Hudspeth et al. | 128/689 |
| 4,206,449 | 6/1980 | Galvin et al. | 340/505 |
| 4,210,905 | 7/1980 | Coons | 340/575 |
| 4,232,682 | 11/1980 | Veth | 128/869 |
| 4,250,888 | 2/1981 | Grosskopf | 128/702 |
| 4,278,968 | 7/1981 | Woods | 340/576 |
| 4,297,685 | 10/1981 | Brainard, II | 340/575 |
| 4,301,808 | 1/1981 | Taus | 128/689 |
| 4,406,289 | 9/1983 | Wesseling et al. | 128/689 |
| 4,489,731 | 12/1984 | Baumberg | 128/687 |
| 4,545,387 | 10/1985 | Balique | 128/687 |
| 4,572,207 | 2/1986 | Yoshimi et al. | 128/706 |

FOREIGN PATENT DOCUMENTS

| | | | |
|---|---|---|---|
| 217422 | 1/1985 | Fed. Rep. of Germany | 128/689 |
| 2052051 | 1/1981 | United Kingdom | 128/689 |

*Primary Examiner*—William E. Kamm
*Assistant Examiner*—David Shay
*Attorney, Agent, or Firm*—Sughrue, Mion, Zinn, Macpeak, and Seas

[57] ABSTRACT

A device for measuring heartbeats of a driver using a multiplicity of optical heartbeat sensors which are dispersed about the rim of steering wheel. Fluctuation (variance) in the period of a heartbeat signal is measured and compared with a reference value to decide the presence or absence of abnormality. The presence of abnormality is signaled by a visual indication and acoustic output. The reference value is set based on the value which was obtained from the actual heartbeat measurement of the driver in a reference value setting mode. The reference value is stored in a non-volatile read-/write memory to be held even when the power is off. The difference in output levels of a light receiving element between when a light emitting element is energized and when it is deenergized, is checked for each heartbeat sensor to decide whether a heartbeat signal has been actually obtained therefrom. As a result of the decision, only those heartbeat sensors actually issuing the heartbeat signals are selectively utilized for making the measurement.

8 Claims, 10 Drawing Figures

VEHICLE-LOADED HEARTBEAT METER

BACKGROUND OF THE INVENTION

The present invention relates to a vehicle-loaded heartbeat meter mounted on a vehicle for measuring heartbeats of a driver or any other passengers, and more particularly to a vehicle-loaded heartbeat meter for comparing the measured result with a reference value to decide the presence or absence of abnormality and then informing the result of the decision.

When driving vehicles, the unhealthy condition of a driver leads to higher probability of accidents. For example, if the driver continues driving for a long time without rest, his health is adversely affected and concentration is reduced with accumulation of fatigue.

Heart rate is one barometer to know the condition of one's health. As a device for measuring heart rate, portable small-sized heartbeat meters have been recently commercialized. This type heartbeat meter is handy to carry anywhere, but has low measurement accuracy. By way of example, even if the driver carries such a heartbeat meter into the vehicle to know the condition of his health during driving, the vehicle must be stopped every time he desires to measure heart rate. More specifically, a typical heartbeat meter of this type comprises a light emitting diode and a photodiode both projected on a board to constitute a reflection type photosensor. In measurement, the sensor is put against the inner surface of a finger and, to avoid an adverse influence of lights coming from the exterior, the sensor and the finger are both covered with a black sponge or the like. Accordingly, the driver can not drive the vehicle with the sensor left fitted on his finger. Furthermore, that type of sensor disables the measurement if the finger is moved during measurement to shift the relative positions of the sensor and the finger, as a result of which the subject (driver) is required to keep quiet.

Meanwhile, it is preferable for a vehicle-loaded heartbeat meter to compare the measured value with a preset value, i.e., normal value and, if the compared result has proved to be abnormal, then inform the driver or any other passengers of the fact to stop driving. In conventional heartbeat meters, the normal value to be compared with the measured value was set using a variable resistor or the like. However, for setting the normal value, this method requires the troublesome operation of previously measuring heart rate in the normal condition by making use of another heartbeat meter with the measured result fixed in mind, and setting a scale on the variable resistor at the resulting value. Furthermore, because heart rate is largely different person by person, setting of the normal value must be updated every time the driver is changed from one to another to alternately drive a car.

Incidentally, UK Patent Applications GB No. 2100850, GB No. 2070240 and GB No. 2052752 are known as prior arts relevant to the present invention.

SUMMARY OF THE INVENTION

The present invention has for a first object to provide a vehicle-loaded heartbeat meter which is capable of simply and precisely setting a normal value, and for a second object to provide a vehicle-loaded heartbeat meter which, even in case for a plurality of persons to utilize the vehicle-loaded heartbeat meter, requires no resetting of the normal value after they have once set their own normal values.

To achieve the above objects, the present invention includes a mode of normal value setting operation in which the heartbeat data measured by the vehicle-loaded heartbeat meter is stored in a predetermined memory as a normal value, i.e., reference value. The memory storing therein the reference value is to be non-volatile so that the reference value once memorized will not be lost upon power-off.

More specifically, when the driver considers his physical condition as normal, he depresses a certain switch, for example, to set a mode of normal value setting operation and then puts his hand against a predetermined heatbeat sensor. Upon this, heartbeat information, i.e., a normal value, of the driver at that time is measured, and the resulting value is stored in the non-volatile memory as a normal value. Accordingly, the operation is very simple and no error occurs in the setting.

With only one reference value set, when a plurality of persons are to utilize the vehicle-loaded heartbeat meter, the reference value is reset every time the user is changed from one to another, whereby the previously memorized reference value is lost. Therefore, a preferred embodiment of the present invention includes a non-volatile memory which is capable of memorizing a plurality of reference values simultaneously, and an identification switch used for discriminating among the users, so that the memory location is selected in response to operation of the identification switch for storage and read-out of the reference value. Even when a plurality of persons are to utilize the vehicle-loaded heartbeat meter, this eliminates the need of resetting after they have once set their own reference values.

Meanwhile, capability of the heartbeat measurement while actually driving requires the provision of a multiplicity of heartbeat sensors along the grip portion of a steering wheel, so that heartbeats may be detected even when the driver grips any position of the steering wheel. However, in attempting to obtain a heartbeat signal from the multiplicity of heartbeat sensors connected in parallel, the noise level due to an influence of lights coming from the exterior is increased and the S/N (signal/noise) ratio is too reduced to perform the detection in some cases, because the number of sensors is small which actually issue heartbeat signals.

Therefore, a third object of the present invention is to provide a vehicle-loaded heartbeat meter which is not susceptible to an influence of light coming from the exterior.

To achieve the above object, a preferred embodiment of the present invention includes; a plurality of heartbeat detection means arranged on a steering wheel or a member supporting the steering wheel and each comprising light emitting means and light receiving means; selection means for selecting a part of the plural heartbeat detection means; informing means for making at least one of visual indication and acoustic output; and electronic control means for controlling the selection means to sequentially select the heartbeat detection means one by one, energizing and deenergizing the light emitting means of the selected heartbeat detection means to measure the difference between an output level of the light receiving means when the light emitting means is energized and an output level of the light receiving means when the light emitting means is deenergized to thereby decide the presence or absence of a heartbeat signal from each of the selected heartbeat detection means, selecting those heartbeat detection means which have been decided as issuing heartbeat signals, measuring at least one of information corresponding to the fluctuation periods of signals output from those selected heartbeat detection means and information on variations thereof, and for energizing the informing means in response to the resulting information.

In this type heartbeat detection means, a light emitted from the light emitting means is received by the light receiving means only when the finger is in contact with the detection means. Stated differently, with the finger contacted with the heartbeat detection means selected sequentially, the light emitted from the light emitting means and reflected from blood or bone in the finger is received by the light receiving means together with lights coming from the exterior, when the light emitting means is energized, and only the exterior lights are received, when the light emitting means is deenergized. Thus, the output level of the light receiving means is changed upon energization and deenergization of the light emitting means in this case. On the other hand, with the finger not contacted with the heartbeat detection means selected sequentially, the level of light received by the light receiving means is determined by the exterior lights only and hence independent of energization and deenergization of the light emitting means.

Accordingly, as a result of comparison in output levels of the light receiving means between when the light emitting means is energized and when it is deenergized, the large difference indicates that the finger is in contact with the selected heart rate detection means, while the small difference indicates that the finger is not contact with the selected heartbeat detection means. Namely, the heartbeat measurement can be performed in case of the large difference, but not performed in case of the small difference. From this reason, the plurality of heartbeat detection means are sequentially selected for such comparative decision and only those heartbeat detection means, which have been decided as issuing heartbeat signals, are selectively employed to detect heartbeats, whereby an influence of the exterior lights is reduced.

BRIEF DESCRIPTION OF THE DRAWINGS

FIGS. 4a, 4b, 4c, 4d and 4e are flow charts showing the schematic operation of a microcomputer CPU shown in FIG. 3a.

DESCRIPTION OF PREFERRED EMBODIMENT

Hereinafter, one embodiment of the present invention will be described with reference to the drawings.

Figure 1:
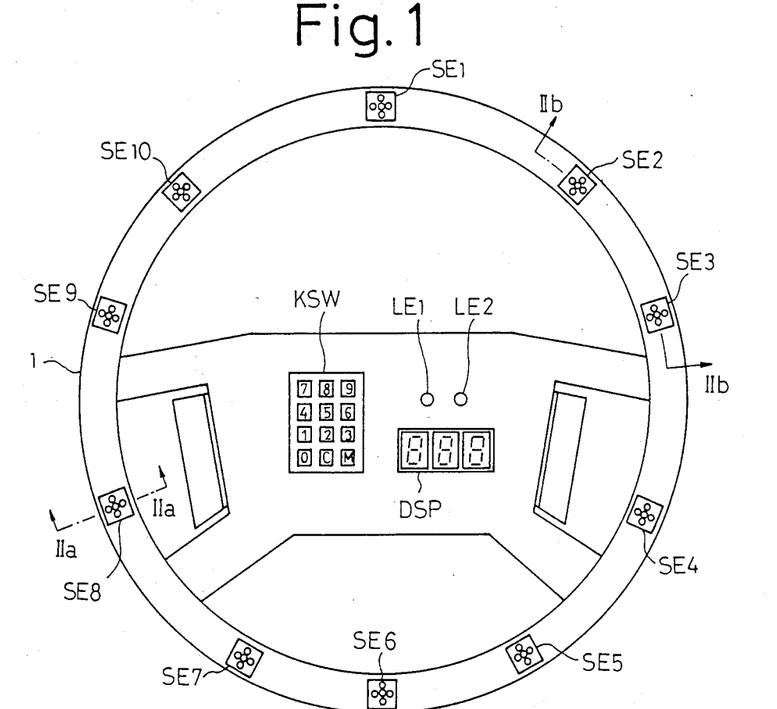
FIG. 1 is a front view showing a steering wheel of the automobile mounting thereon a vehicle-loaded heartbeat meter according to one embodiment.

FIG. 1 shows a steering wheel 1 of the automobile mounting thereon a vehicle-loaded heartbeat meter according to one embodiment. Referring to FIG. 1, in this embodiment, ten heartbeat sensors SE1-SE10 are arranged on the circumference of the steering wheel 1 with spacings therebetween. On a central panel of the steering wheel 1, there are provided a numeral display DSP for indicating heart rate, a ten-key switch KSW for inputting identification codes, etc., a light emitting diode LE1 for indicating the timing of heartbeat, and a light emitting diode LE2 for indicating the non-setting of reference value. The ten-key switch KSW also includes a key switch "M" for designating a mode of normal value setting.

Figure 2A:
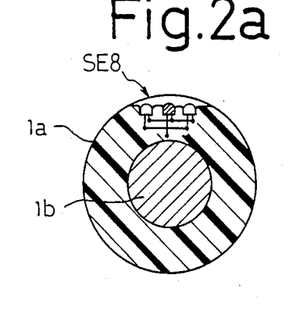
FIGS. 2a and 2b are sectional views taken along the line IIa—IIa and the line IIb—IIb in FIG. 1, respectively.
Figure 2B:
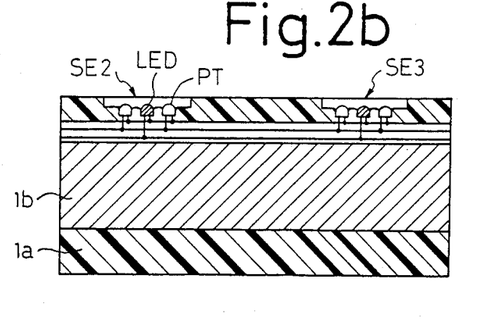

The heartbeat sensors are each comprised of a single infrared light emitting diode LED disposed at the center thereof and four infrared phototransistors PT disposed to surround the LED, these elements having their optical axes all directed in the same direction, i.e., upwardly of the steering wheel 1. As shown in FIGS. 2a and 2b, the steering wheel 1 comprises an iron core 1b and a resin material 1a covering the iron core, and each heartbeat sensor is buried in the resin material 1b except for the light emitting surface and the light receiving surface thereof. Lead wires from the heartbeat sensors are led through the resin material 1a to reach a pad at the center of the steering wheel 1.

Figure 3A:
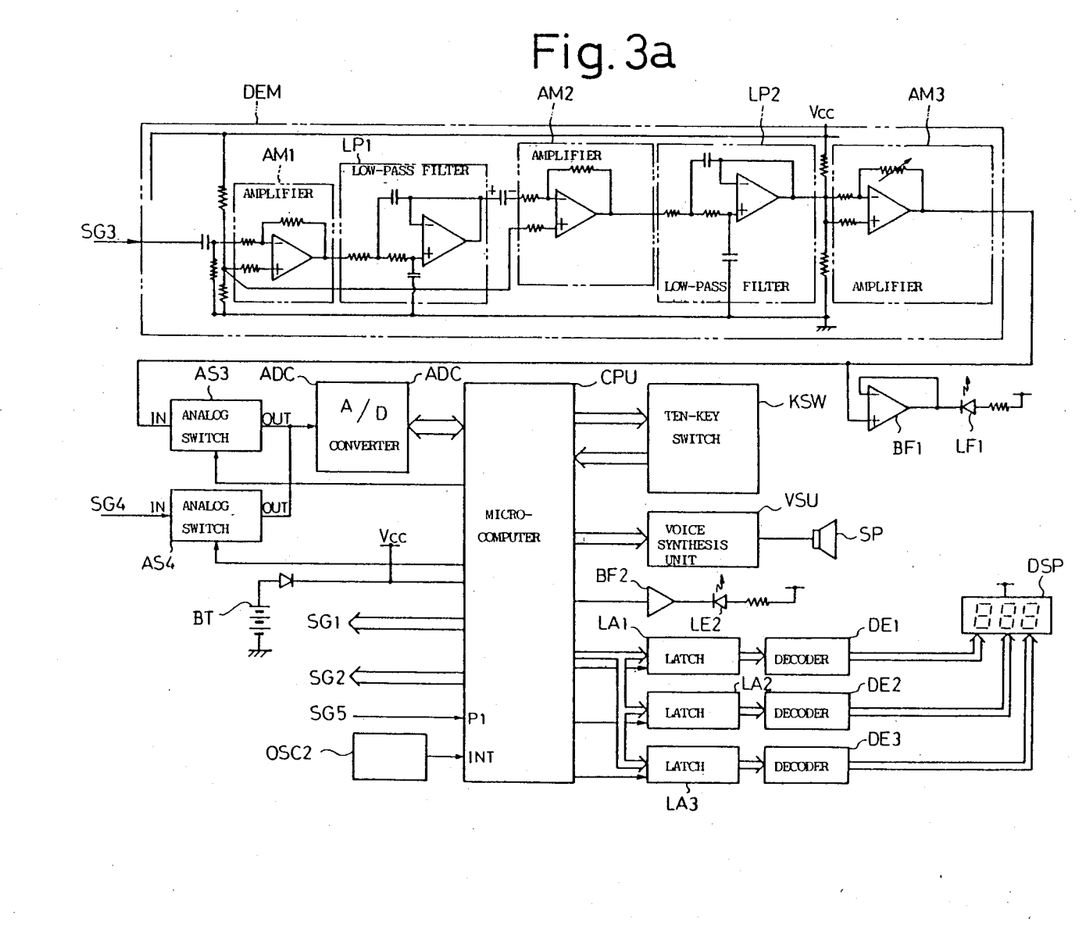
FIGS. 3a and 3b are block diagrams showing the construction of the vehicle-loaded heartbeat meter fitted in the steering wheel of FIG. 1.
Figure 3B:
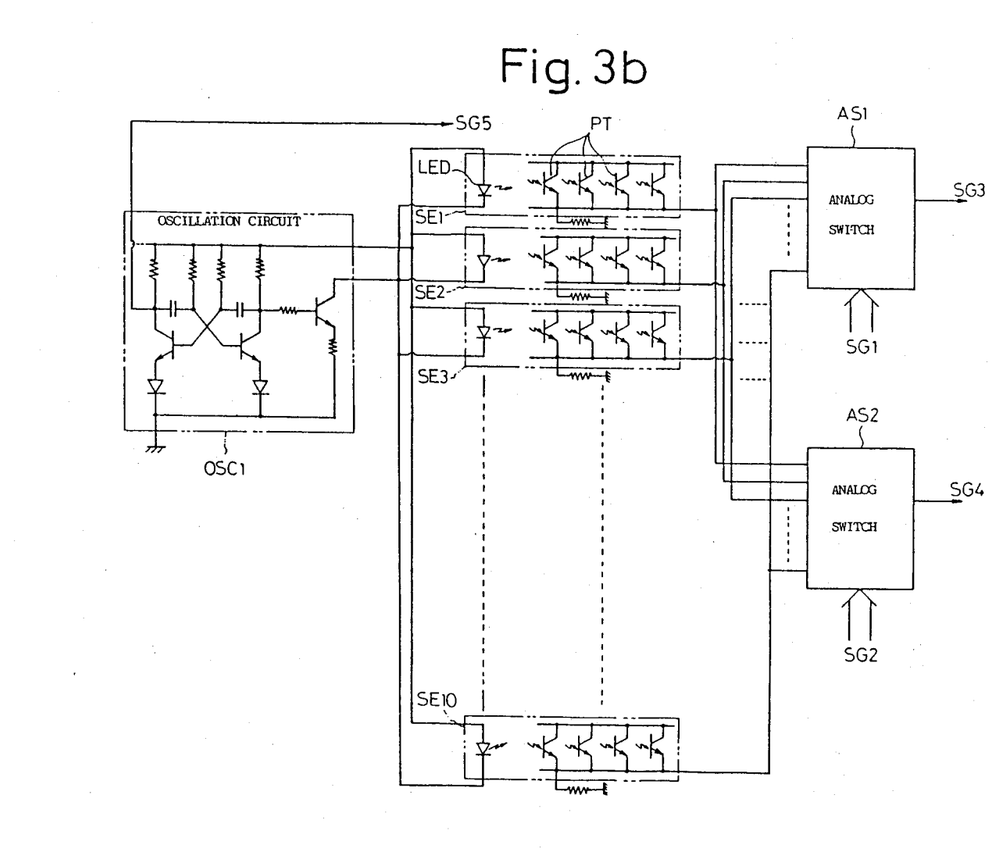

FIGS. 3a and 3b show an electric circuit of the vehicle-loaded heartbeat meter, most of which is incorporated in the central pad of the steering wheel 1 of FIG. 1. Referring to FIG. 3b, the light emitting diodes of the heartbeat sensors SE1-SE10 are connected in parallel to each other and also connected to an output terminal of an oscillation circuit OSC1. In this embodiment, the oscillation circuit OSC1 outputs a square wave signal with constant period of 1 KHz. Thus, the light emitting diode of each heartbeat sensor is lit up and put out repeatedly with period of 1 KHz. The duty cycle is 50%.

The phototransistors PT of the heartbeat sensors are connected in parallel to each other, each PT having one end connected to a power source and the other end connected to input terminals of analog switches AS1 and AS2. The analog switches AS1 and AS2 comprise each ten analog switching elements which have their output terminals commonly connected together. Connected to input terminals of those elements are the output terminals of the heartbeat sensors. Control signals SG1 and SG2 output from a microcomputer CPU are respectively applied to conduction control terminals of the analog switches AS1 and AS2 (each terminal including 10 lines). An output terminal (SG3) of the analog switch AS1 is connected to an input terminal of an analog switch AS3 through a demodulator DEM, and an output terminal (SG4) of the analog switch AS2 is connected to an input terminal of an analog switch AS4. Output terminals of the analog switches AS3 and AS4 are commonly connected together and then connected to an analog input terminal of an analog/digital converter ADC. The analog/digital converter ADC is in turn connected to the microcomputer CPU.

The principles of heartbeat detection will now be described briefly. When one's finger is positioned to face any one of the heartbeat sensors, the light reflectance at that portion (finger) is varied depending on the flow rate of blood, i.e., heartbeat. Accordingly, a heartbeat signal can be obtained by directing a light of predetermined intensity upon that portion, receiving the reflected light therefrom and deciding a level of the received light. In this embodiment, because the light emitting diode LED is lit up and put out repeatedly with period of 1 KHz, an electric signal of 1 KHz amplitude-modulated with the heartbeat signal is obtained at the output terminal of the heartbeat sensor.

The demodulator DEM shown in FIG. 3a functions to demodulate the original heartbeat signal from the above modulated signal. The demodulator DEM comprises, in this embodiment, amplifiers AM1, AM2 and AM3 and low-pass filters LP1 and LP2. A light emitting diode LE1 is connected to an output terminal of the demodulation DEM through a buffer BF1. Thus, the light emitting diode LE1 is turned on and put out in response to the heartbeat signal.

As a result, the heartbeat signal is applied to the analog/digital converter ADC with the analog switches AS3 and AS4 turned on and off, respectively, while the modulated signal is applied to the ADC with the analog switches AS3 and AS4 turned off and on, respectively.

Connected to an external interrupt request terminal INT of the microcomputer CPU is an oscillator OSC2. The oscillator OSC2 outputs a square wave signal of 500 Hz. Therefore, the microcomputer CPU implements the external interrupt process for each 2 msec as described later.

Connected to a power source line of the microcomputer CPU is a battery BT through a diode for preventing the reverse current. The battery BT is adapted to supply an electric power sufficient to hold the content of a memory within the CPU, when a main power source of the microcomputer CPU is cut off. Thus, the internal memory (RAM) of the microcomputer CPU operates as a non-volatile memory.

To other ports of the microcomputer CPU, there are connected the ten-key switch KSW, a voice synthesis unit VSU, a buffer BF2, and latches LA1, LA2 and LA3. A speaker SP is connected to an output terminal of the voice synthesis unit VSU, a light emitting diode LE2 is connected to an output terminal of the buffer BF2, and decoders DE1, DE2 and DE3 are respectively connected to output terminals of the latches LA1, LA2 and LA3. More concretely, the decoders DE1, DE2 and DE3 are decoder drivers for 7-segment displays, to output terminals of which is connected the numeral display DSP.

FIGS. 4a, 4b, 4c, 4d and 4e show schematic operation of the microcomputer CPU shown in FIG. 3a. Operation of the microcomputer CPU will be described below by referring to these drawings.

Figure 4A:
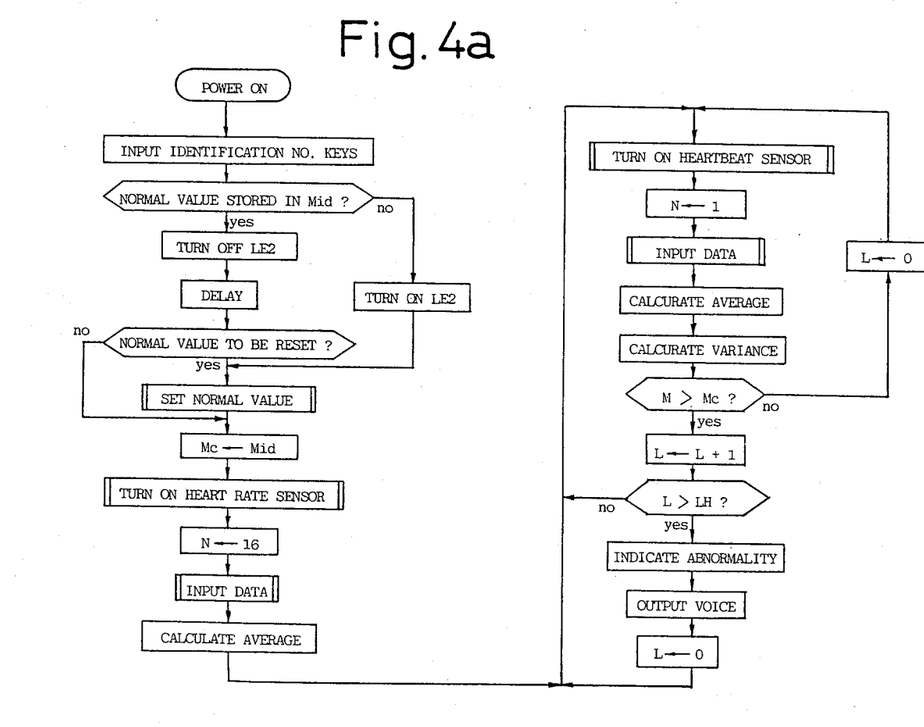
Figure 4B:
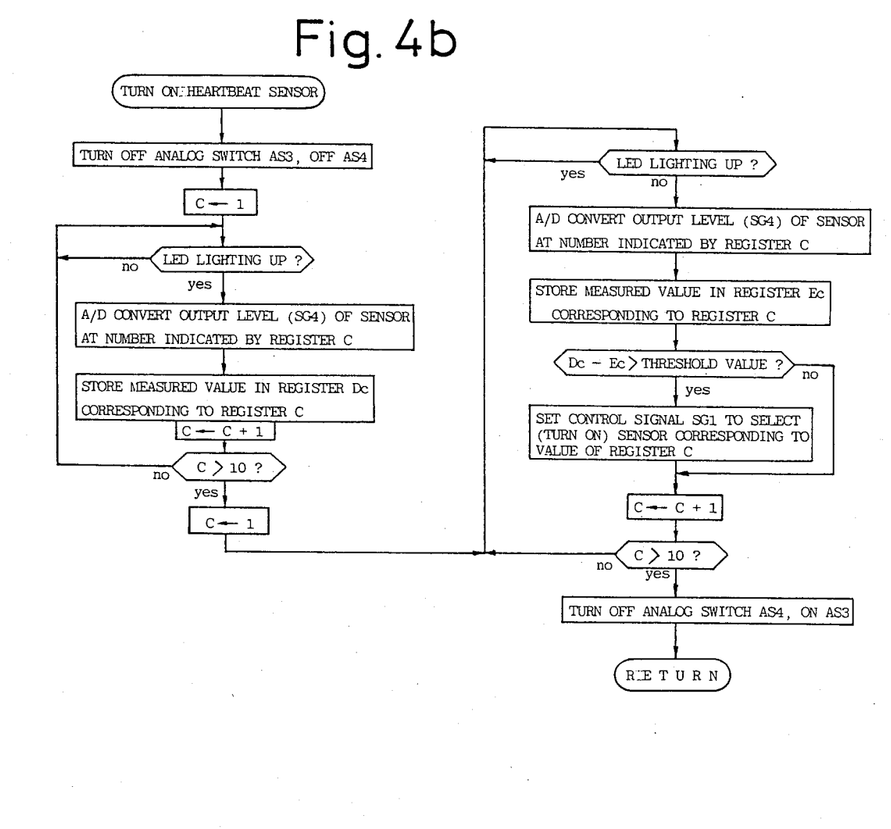
Figure 4C:
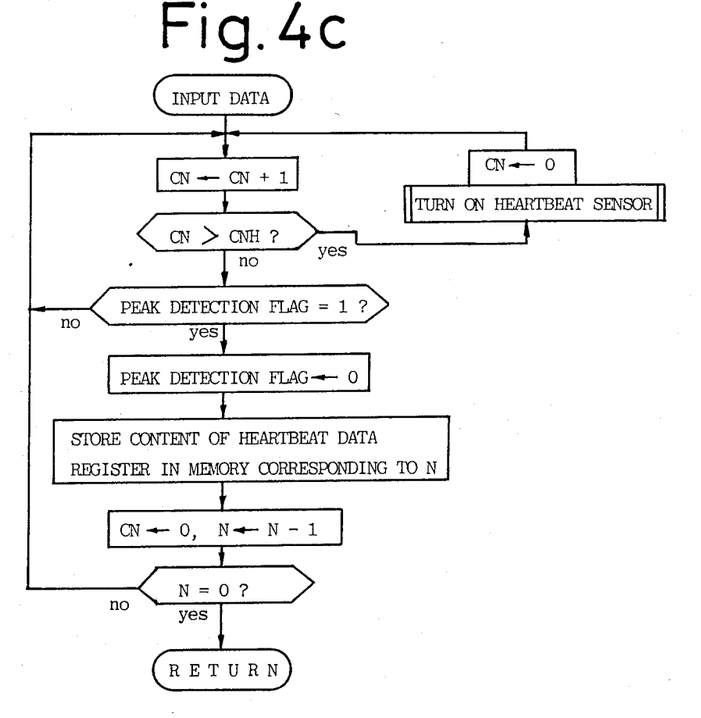
Figure 4D:
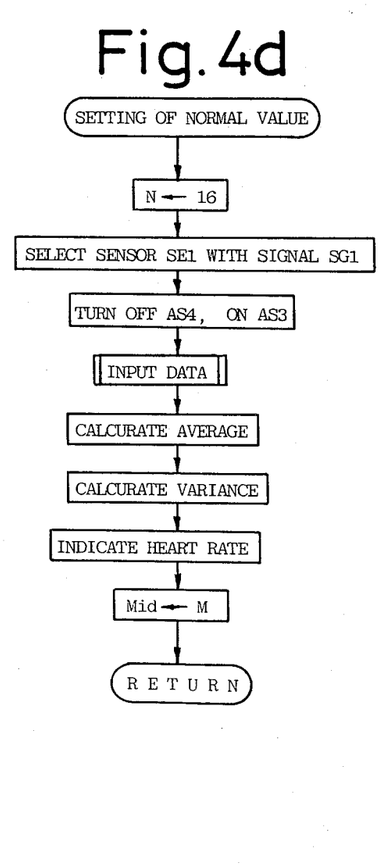
Figure 4E:
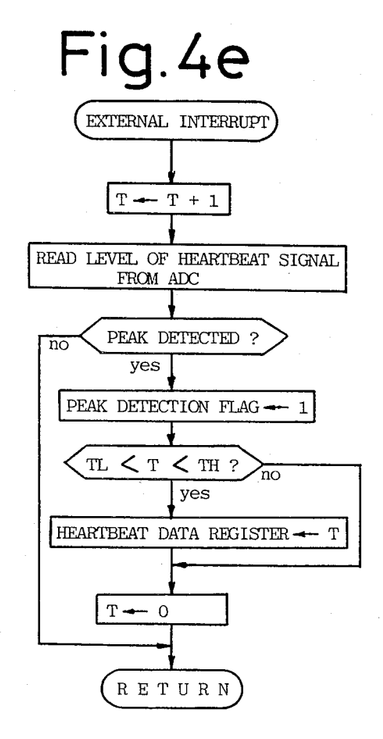

When powered on, i.e., when an ignition key switch is turned on, the microcomputer waits for input of the identification number. In this embodiment, any desirous numerical code of three digits is input. There are provided memories to store reference values for five persons by way of example, and particular numerical codes are allocated to the respective memories. When some numerical code is input, the allocated memory is retrieved. If no relevant memory is found, it is checked whether or not there exists any memory to which the numerical code has not yet been allocated. If such a memory is present, the input numerical code is allocated to that memory. Otherwise, it waits for input of the identification number again. Depressing of a key "C" clears the content of the memory for a particular person.

If the memory allocated with the input numerical code is found, it is checked whether or not a normal value is already stored in that memory. If already stored, the light emitting diode LE2 is put out, and otherwise, the LE2 is lit up. In case a normal value is already stored, after waiting for a short time, it is checked whether or not resetting of a normal value is instructed. Namely, if the key "M" on the ten-key switch KSW is depressed following input of the numerical code, this is considered as an instruction for resetting of a normal value.

In both cases where a normal value is not yet stored in the memory and where resetting of a normal value is instructed, a "normal value setting" subroutine is then implemented.

In the "normal value setting" subroutine, after setting 16 in a register N, the control signal SG1 is set to cause the analog switch AS1 to select an output of the sensor SE1. Also, the analog switches AS4 and AS3 are turned off and on, respectively. After completion of the above setting, the heartbeat signal obtained at the output terminal of the sensor SE1 (i.e., output of the demodulator) is applied to the analog/digital converter ADC.

Next, a "data input" subroutine will be implemented. In the "data input" subroutine, in summary, the data on the period between successive peaks of the heartbeat signal (so-called R-R interval), which has been loaded in the heartbeat data register, is stored in the memory corresponding to the content of the resistor N for each detection of a peak of the heartbeat signal. Simultaneously, the content of the register N is decremented by one. The above operation is repeated until the content value has become equal to zero.

Whether or not a peak of the heartbeat signal has been detected can be known by checking a peak detection flag which is set upon an external interrupt later described. Because detachment of the hand from the heartbeat sensor SE1 during measurment of data leads to the incorrect data, a counter CN measures a time period in which the peak detection flag is set at 0 and, if the measured value exceeds a predetermined value CNH, the process is interrupted to implement a "heartbeat sensor-on" subroutine later described. In this embodiment, with 16 preset in the register N, after the process of the "data input" subroutine, the period data for 16 heartbeats are stored in 16 memories, respectively. Both the average and the variance of heartbeat periods are determined using those period data. The variance or variations can be calculated from the following equation by assuming for the period data of predetermined samples to be S:

$$\text{Variance} = \text{Average of } S^2 - (\text{Average of } S)^2$$

Also, a reciprocal number of the average of heartbeat periods, i.e., heart rate, is calculated and then indicated on the numeral display DSP. The resulting variance M is stored in a reference value memory Mid selected corresponding to the numerical code of three digits. With this, setting of a reference value or normal value for a particular person corresponding to the numerical code input at that time is completed. Thereafter, the reference value can be updated at anytime by inputting the corresponding numerical code.

The description will be continued by returning to FIG. 4a. The content of the memory Mid storing therein a normal value for the relevant person is transferred to a reference value register Mc, and the "heartbeat sensor-on" subroutine is now implemented.

In the "heartbeat sensor-on" subroutine, in summary, those sensors among the total ten heartbeat sensors from which heartbeat signals can be actually taken out are searched and the heartbeat signals from those sensors are selectively applied to the input terminal of the analog/digital converter ADC.

More specifically, the analog switches AS3 and AS4 are first turned off and on, respectively. This causes an output of the analog switch AS2, i.e., the modulated heartbeat signal SG4, to be input to the ADC. Then, after setting 1 in a register C, the microcomputer waits for the light-up timing of the heartbeat sensor. This timing can be decided by viewing the level of a signal SG5 input to a port P1 from the oscillation circuit OSC1.

When the light-up timing is reached, the control signal SG2 for the analog switch AS2 is set corresponding to the value of the register C, so that an output of the predetermined heartbeat sensor (e.g., output of the SE1 with the register C set at 1) is selected and subjected to A/D conversion. The converted data is loaded into a register Dc corresponding to the value of the register C. Note that there are provided ten registers Dc. The value of the register C is then incremented by one. The above operation is repeated until the resulting value has reached 10.

At the time after completion of the foregoing process, the output levels of the heartbeat sensors SE1-SE10 when lit up are stored in those ten registers Dc, respectively. Next, after setting 1 in the register C again, the microcomputer waits for the lights-out timing of the heartbeat sensor. This timing can be also decided by viewing the level of the port P1.

When the lights-out timing is reached, the control signal SG2 for the analog switch AS2 is set corresponding to the value of the register C, so that an output of the predetermined heartbeat sensor (e.g., output of the SE1 with the register C set at 1) is selected and subjected to A/D conversion. The resulting measured data is stored in a register Ec corresponding to the value of the register C. The difference of. contents between the registers Dc and Ec selected in accordance with the current value of the register C is compared with a predetermined threshold value. If the hand is in contact with the heartbeat sensor selected, the signal level exhibits a large difference between the light-up timing and the lights-out timing of the heartbeat sensor, but if that heart rate is in an open state, the signal level exhibits no substantial difference between the light-up timing and the lights-out timing. Accordingly, if the difference of contents between the registers Dc and Ec is larger than a predetermined value, this means that the body part is in contact with the corresponding heartbeat sensor and a heartbeat signal can be taken out therefrom.

Therefore, the control signal SG1 is set to turn on the sensor when the difference of Dc - Ec is larger than a threshold value, and to turn off the then sensor when it is smaller than a threshold value. The content of the register C is then incremented by one. The above operation is repeated until the resulting value has reached 10. After implementing the foregoing process for all of the heartbeat sensors SE1-SE10, the analog switches AS4 and AS3 are turned off and on, respectively.

In this state, output signals from all the usable heartbeat sensors selected in the repeated foregoing process are applied to the analog input terminal of the analog/digital converters ADC through the demodulator DEM and the analog switch AS3.

After completion of the "heartbeat sensor-on" subroutine, the average value is calculated by setting 16 in the register N and implementing the before-mentioned "data input" subroutine. In other words, the heartbeat data for 16 heartbeats are measured and the average value thereof is calculated.

Next, the microcomputer comes into the loop process. This loop process proceeds as follows; to implement the "heartbeat sensor-on" subroutine, set 1 in the register N, implement the "data input" subroutine, calculate both the average and the variance, and to compare the resulting variance M with the reference value Mc. Stated differently, for each loop process, the period data for new one heartbeat is input to calculate both the average and variance of the heartbeat periods for decision of the result.

When the variance M is relatively small (less than Mc), the content of the register L is cleared and the process is continued, but when the variance M is above the predetermined value Mc, the value of the register L is incremented by one. If the value of the register L exceeds a predetermined value LH, i.e., if the state that the variance is larger than the normal value continues for a relatively long predetermined time, this is decided as abnormality to give an abnormality indication (by energizing the light emitting diode LE2) and issue a voice output of "Take a Rest" from the voice synthesis unit VSU. Thereafter, the content of the register L is cleared and the process is continued.

The "external interrupt" process will now be described. In this embodiment, the "external interrupt" process is implemented periodically for each 2 msec in response to a signal from the oscillator OSC2. In this process, the content of a register T for measuring period data is first incremented by one. Next, the level of a heartbeat signal is read from the analog/digital converter ADC to decide from the read result whether or not a peak of the heartbeat signal has been detected. More specifically, as a result of comparison with the data obtained from the preceding "external interrupt" process, detection of peak is decided if the current data is equal to or smaller than the preceding data.

When the peak is not detected, the process is ended immediately. When the peak is detected, the peak detection flag is first set to 1. It is then checked whether or not the content of the register T is within a predetermined range. If within a predetermined range, the data value is stored in the heartbeat data register. Finally, the value of the register T is cleared to 0.

Although in the above-mentioned embodiment the decision was made based on only the variance of heartbeat periods, heart rate may be used for such decision. Also, although in the illustrated embodiment ten heartbeat sensors were dispersely arranged on the steering wheel, the number of the sensors can be increased, or it is enough to provide a single sensor if the heartbeat measurement is to be made on the automobile only while stopping. Further, although in the embodiment one of the heartbeat sensors used for the measurement was commonly employed for setting a reference value, a particular dedicated sensor may be provided. Furthermore, although in the embodiment the numerical code was input using a ten-key switch to select the corresponding memory for a reference value, the ten-key switch may be replaced by a plurality of switches which are provided corresponding to the individual memories one to one.

As fully described above, according to the present invention, it becomes possible to precisely set a reference value for making decision with simple operation. As shown in the embodiment, since a plurality of heartbeat detection means are arranged on the steering wheel and those heartbeat detection means from which heartbeat signals can be actually obtained are selectively utilized for the measurement, the S/N ratio of the signals is improved and a malfunction due to lights coming from the exterior can be avoided.

What I claim is:

1. A vehicle-loaded heartbeat meter comprising:
   plural heartbeat detection means, including optical detection means, on a steering wheel or a member supporting said steering wheel;
   switch means for enabling entry of user identification information;
   informing means for providing at least one of a visual indication and an acoustic outout; and electronic control means connected to said plural heartbeat detection means, said switch means, and said informing means, including non-volatile memory means adapted to hold the content stored therein even when powered off,
   selection means for selecting at least one of said plural heartbeat detection means having a difference between an output level of the heartbeat detection means when the heartbeat detection means is energized and an output level of the heartbeat detection means when the heartbeat detection means is deenergized larger than a predetermined level.
   processing means for generating at least one of information corresponding to the fluctuation periods of signals output from said heartbeat detection means selected by said selection means and information on variations thereof,
   storing control means for storing said information generated from said processing means into said non-volatile memory means when said switch means is turned on,
   comparing means for comparing signal output from said heartbeat detection means selected by said selection means with said information stored in said non-volatile memory means, and
   means for energizing said informing means in response to the result of comparing of said comparing means.

2. A vehicle-loaded heartbeat meter according to claim (1), wherein said non-volatile memory means includes a plurality of storage areas for storing therein a plurality of reference values, said switch means includes identification switch means comprising a plurality of switches adapted to identify a plurality of users individually, and said electronic control means further includes means for selecting a storage area of said non-volatile memory means for storing and reading in response to operation of said identification switch means.

3. A vehicle-loaded heartbeat meter according to claim (1), wherein said electronic control means further includes means for intermittently energizing said plural heartbeat detection means for sequentially switching said plural heartbeat detection means, means for comparing the difference between a signal level obtained at the time when energized and a signal level obtained at the time when deenergized with a predetermined threshold value for deciding the presence or absence of a heartbeat signal issued from each of said heartbeat detection means, and wherein selection means includes means for automatically selecting those heartbeat detection means which issue the heartbeat signals for the heartbeat measurement.

4. A vehicle-loaded heartbeat meter according to claim (1), wherein said selection means includes means for sequentially selecting all of said plural heartbeat detection means one by one, and wherein said electronic control means includes means for intermittently energizing said heartbeat detection means selected, and means for comparing the difference between a signal level obtained at the timing when energized and a signal level obtained at the timing when deenergized with a predetermined threshold value for deciding the presence or absence of a heartbeat signal issued from each of said heartbeat detection means, and wherein said selection means includes means for automatically selecting all those heartbeat detection means which issue the heartbeat signals for the heartbeat measurement.

5. A vehicle-loaded heartbeat meter according to claim (1), wherein said optical detection means comprises light emitting means and light receiving means disposed near said light emitting means to have the optical axis thereof directed substantially in the same direction as that of said light emitting means.

6. A vehicle-loaded heartbeat meter comprising:
   plural heartbeat detection means arranged on a steering wheel or a member supporting said steering wheel, each of said plural heartbeat detection means including light emitting means and light receiving means;
   switch means for enabling entry of user indentification information;
   informing means for providing at least one of a visual indication and an acoustic output; and
   electronic control means, connected with said plural heartbeat detection means, said switch means, and said informing means, including:
   non-volatile memory means adapted to hold the content stored therein even when powered off;
   selection means for selecting at least one of said plural heartbeat detection means;
   first processing means for controlling said selection means to sequentially select said plural heartbeat detection means one by one, for controlling energizing and deenergizing of said light emitting means of the selected heartbeat detection means, for comparing the difference between an output level of said light receiving means of said selected heartbeat detection means when said light emitting means is energized and an output level of said light receiving means of said selected heartbeat detection means when said light emitting means is deenergized with a predetermined threshold value to decide the presence or absence of a heartbeat signal issued from the selected heartbeat detection means, and for controlling said selection means to select those heartbeat detection means which issue the heartbeat signals as a result of said decision;
   second processing means for generating at least information on the fluctuation periods of signals output from those selected heartbeat detection means and information on variations thereof, and for storing the generated information in said non-volatile memory means as a reference value when said switch means is turned on; and
   third processing means for generating at least one of information on the fluctuation periods of signals output from those selected heartbeat detection means and information on variations thereof, for comparing the information generated by the third processing means with said reference value stored in said non-volatile memory means, and for energizing said informing means in accordance with result of the comparing.

7. A vehicle-loaded heartbeat meter according to claim (6), wherein said non-volatile memory means includes a plurality of storage areas for storing therein a plurality of reference values, said switch means includes identification switch means comprising a plurality of switches adapted to identify a plurality of users individually, and wherein said electronic control means includes means for selecting a storage area of said nonvolatile memory means for storing and reading in response to operation of said identification switch means.

8. A vehicle-loaded heartbeat meter according to claim 6, wherein each said plural heartbreak detection means comprises light emitting means and light receiving means disposed near said light emitting means to have the optical axis thereof directed substantially in the same direction as that of said light emitting means.

* * * * *